United States Patent [19]
Granz et al.

[11] Patent Number: 5,735,796
[45] Date of Patent: Apr. 7, 1998

[54] THERAPY APPARATUS WITH A SOURCE OF ACOUSTIC WAVES

[75] Inventors: Bernd Granz, Oberasbach; Guenther Winkelmann, Herzogenaurch, both of Germany

[73] Assignee: Siemens Aktiengesellschaft, Munich, Germany

[21] Appl. No.: 754,152

[22] Filed: Nov. 22, 1996

[30] Foreign Application Priority Data

Nov. 23, 1995 [DE] Germany .................. 195 43 825.6

[51] Int. Cl.$^6$ ........................................................ A61B 8/00
[52] U.S. Cl. ........................................ 600/439; 601/2
[58] Field of Search ................... 128/660.01, 660.02, 128/660.03, 660.08, 661.01; 601/1, 2, 3, 4; 604/22

[56] References Cited

U.S. PATENT DOCUMENTS

| | | |
|---|---|---|
| 4,697,588 | 10/1987 | Reichenberger . |
| 4,821,730 | 4/1989 | Wurster et al. . |
| 4,928,672 | 5/1990 | Grasser et al. . |
| 5,471,988 | 12/1995 | Fujio et al. ............ 128/660.03 |
| 5,526,815 | 6/1996 | Granz et al. .......... 128/660.03 |
| 5,558,092 | 9/1996 | Unger et al. .......... 128/660.03 |
| 5,624,382 | 4/1997 | Oppelt et al. ................ 601/2 |

FOREIGN PATENT DOCUMENTS 0 194 897  3/1991  European Pat. Off. .

OTHER PUBLICATIONS

"The Disintegration of Urinary Calculi by Piezioelectrically Generated High–Energy Sond Pulses, Physical Foundations and Experimental Investigations," Riedlinger et al., Urologe, vol. 25, (1986), pp. 188–192.

"Electromagnetic Shock–Wave Lithotripsy of Gall–Stones: Preliminary Clinical Results," Neuhaus et al., Dtsch. med. Wschr., Viol, 115 (1990), PP. 123–128.

"Dreidimensionale Ultraschalldarstellung," Sohn et al., Dtsch. med. Wschr. vol., 117 (1992) pp. 467–472.

Primary Examiner—George Manuel
Attorney, Agent, or Firm—Hill & Simpson

[57] ABSTRACT

A therapy apparatus with a source of therapeutic acoustic waves, an ultrasound locating system with a diagnostic ultrasound transducer that emits a diagnostic ultrasound beam whose central ray is displaceable such in a scanning surface so that it scans a body slice of a subject to be treated achieves an improved image quality of the ultrasound images by the scanning surface being continually displaced slightly relative to the source during the generation of ultrasound images.

16 Claims, 4 Drawing Sheets

THERAPY APPARATUS WITH A SOURCE OF ACOUSTIC WAVES

BACKGROUND OF THE INVENTION

FIELD OF THE INVENTION

German OS 35 43 867, corresponding to U.S. Pat. No. 4,821,730 discloses a therapy apparatus having a source of acoustic waves and a diagnostic ultrasound transducer belonging to an ultrasound locating means for generating and receiving diagnostic ultrasound waves. The ultrasound transducer emits ultrasound waves in the form of a diagnostic ultrasound beam whose central ray moves in a scan surface or area so that a body slice of a subject to be treated can be scanned by the ultrasound beam. A middle of the body slice constitutes the scanning surface. An ultrasound image-generating unit that interacts with the diagnostic ultrasound transducer for generating ultrasound images.

During the ultrasound image generation in this known apparatus, the diagnostic ultrasound transducer is rigidly connected to the source of therapeutic acoustic waves. It is generally assumed that this is necessary since the ultrasound image generated by the ultrasound transducer and the ultrasound image-generating unit contains a graticule for the locating, and a reliable locating is only possible when the spatial position of the ultrasound transducer, and thus the position of the scanning surface, is known relative to the source of therapeutic acoustic waves.

It has been shown that the ultrasound images generated with the diagnostic ultrasound transducer and the ultrasound image-generating unit of such a therapy apparatus is considered poorer in terms of perception than ultrasound images obtained by means of conventional ultrasound examinations.

SUMMARY OF THE INVENTION

An object of the present invention is to provide a therapy apparatus of the type described above wherein ultrasound images that have an improved image quality, at least with respect to subjective perception, can be generated with the diagnostic ultrasound transducer and the ultrasound imaging-generating unit.

This object is inventively achieved in a therapy apparatus having a source of therapeutic acoustic waves, a diagnostic ultrasound transducer for generating and for receiving diagnostic ultrasound waves that emits ultrasound waves in the form of a diagnostic ultrasound beam whose central ray moves in a scanning surface that a body slice of a subject to be treated can be scanned by the ultrasound beam. The scan surface has a midde surface which corresponds to the scanning surface, i.e. is identical with the scanning surface. An ultrasound image-generating unit interacts with the diagnostic ultrasound transducer for generating ultrasound images. Lastly, the apparatus includes adjustment means for during the generation of ultrasound images, displacing the scanning surface relative to the source of therapeutic acoustic waves such that the maximum displacement of the scanning surface relative to a neutral position of the scanning surface does not significantly exceed twice the image resolution of the ultrasound images measured in the direction of the offset.

The diagnostic ultrasound transducer and the ultrasound image-generating unit in the aforementioned known therapy apparatus generate a stationary ultrasound image because of the stationary arrangement of the ultrasound transducer relative to the source of therapeutic acoustic waves. The scanning surface in the inventive therapy apparatus is not stationery with respect to the source of therapeutic acoustic waves during the generation of the ultrasound image. A stationary ultrasound image is thus not generated. On the contrary, a sequence of slightly differing ultrasound images is generated, similar to the case of a standard ultrasound examination wherein the ultrasound head of the ultrasound diagnostic apparatus is guided by the hand of the physician that, naturally, moves slightly. With respect to the subjectively perceptible image quality, the stationary ultrasound images as generated by the therapy apparatus of the prior art, differ from the ultrasound images of the inventive therapy apparatus in about the same way as an individual photo taken from an ultrasound examination or a video frame taken from a video film, i.e. an excerpt of a sequence of slightly different ultrasound images from the same ultrasound examination.

The low image quality of the stationary ultrasound images produced by a therapy apparatus of the prior art due to the presence of stationary and thus immobile speckles (interference phenomena) in the stationary ultrasound image that superimpose on the ultrasound image, as well as the usual, low resolution of ultrasound images (a number of millimeters up to 1 cm) that does not allow an interconnected display of the imaged structures, for example organs. The improved image quality of the inventive therapy apparatus is because as a result of the displacement of the scanning surface during the generation of ultrasound images, the speckle pattern changes from ultrasound image to ultrasound image and neither a stationary ultrasound image nor a stationary speckle image can thus arise. As a result, the contrast between the useful image and the speckle image becomes better. Since the displacement of the scanning surface does not significantly exceed twice the resolution of the ultrasound images measured in the direction of the displacement, the same body slice, so to speak, is always displayed despite the displacement of the scanning surface but a stationary ultrasound image is not generated. The contours of the displayed structures are thus always located at nearly the same place in the ultrasound images, so that the human optical perception can connect the contours of the structures to form continuous lines, thus enhancing the subjectively perceived image quality.

Since, as already mentioned, the maximum displacement of the scanning surface as a maximum does not significantly exceed twice the resolution of the ultrasound images measured in the direction of the displacement, the precision of the locating is not disadvantageously influenced despite the displacement of the scanning surface. Preferably, the adjustment means effect the displacement of the scanning surface relative to the source of therapeutic acoustic waves in such a way that the different scanning surfaces are least partially contained within the body slice belonging to the neutral position of the scanning surface.

The displacement of the scanning surface relative to the source of therapeutic acoustic waves, moreover, can ensue in the form of a continuous or step-by-step movement.

When the ultrasound transducer is fashioned as phased array (arrangement of ultrasound transducer elements drivable phase-offset), there is the possibility of effecting the displacement of the scanning surface electronically. Otherwise, the displacement of the scanning surface must be effected by displacement of the ultrasound transducer relative to the source of therapeutic acoustic waves.

It should be noted that adjustability of an ultrasound transducer relative to the source of therapeutic acoustic waves is present in the therapy apparatus of the aforementioned German OS 35 43 867 (also see "Die Zertrümmerung von Nierensteinen durch piezoelektrisch erzeugte Hochenergie-Schallpulse", Riedlinger et al., Urologe A (1986), 25:188–192, as well as "Elektromagnetische Stosswellenlithotripsie von Gallenblasensteinen", Neuhaus et al., Dtsch. med. Wschr. 115 (1990), 123–128, Georg Thieme Verlag Stuttgart-New York). This adjustability, however, only serves the purpose of allowing the orientation of the ultrasound transducer to be adapted particular anatomical conditions. The ultrasound transducer is stationary relative to the source of therapeutic acoustic waves during the generation of the ultrasound images serving for locating, so that, apart from movements on the part of the subject to be treated, stationary ultrasound images are generated.

This applies analogously to a therapy apparatus disclosed in European Application 0 194 897 wherein the ultrasound transducer is sequentially moved in order to register different two-dimensional ultrasound images that are then combined to form a three-dimensional ultrasound image. This technique, moreover, is also known from standard ultrasound diagnostics (in this respect, see "Dreidimensionale Ultraschalldarstellung", Sohn et al., Dtsch. med. Wschr. 117 (1992), 467–472, George Thieme Verlag Stuttgart-New York).

In an embodiment of the invention wherein the adjustment means displace the scanning surface by steps, the ultrasound image-generating unit generates the ultrasound images with an image repetition rate that is selected such that an ultrasound image represents more than one depth position of the scanning surface. Compared to the situation wherein only one ultrasound image is generated per step of the displacement, an image quality that is even more improved is assured as a result.

The displacement of the scanning surface can be realized especially simply in technological terms when the adjustment means displace the position of the scanning surface relative to the source of therapeutic acoustic waves in the sense of an oscillating motion, according to a preferred embodiment of the invention. For an optimally good image quality, the ultrasound image-generating unit should generate the ultrasound images with an image repetition rate that is at least equal to the frequency of the oscillating motion in this case.

Especially slight effects on the precision of the locating device in the case of an oscillating motion are achieved when the oscillating motion ensues around the neutral position of the scanning surface as middle position.

According to a further version of the invention the adjustment means displace the scanning surface relative to the source of therapeutic acoustic waves in substantially straight-line motion and/or of a swivel motion.

The ultrasound image generation takes on an especially simple form when the scanning surface is substantially planar in another embodiment of the invention. In this case, the displacement of the scanning surface takes on an especially simple form when it proceeds in a preferably straight-line motion substantially parallel to the scanning surface belonging to the neutral position. The straight-line motion, however, can also proceed in a direction substantially transverse to the scanning surface belonging to the neutral position.

The displacement of the scanning surface can likewise be realized in a technologically simple way when it ensues in a swivel motion around an axis that proceeds parallel to the scanning surface belonging to the neutral position or substantially transverse to this scanning surface.

For a good precision of the locating, the scanning surface can proceed through the focus zone at least for the neutral position, in that instance wherein the source of therapeutic acoustic waves generates therapeutic acoustic waves that are focussed onto a focus zone.

DESCRIPTION OF THE PREFERRED EMBODIMENTS

Figure 1:
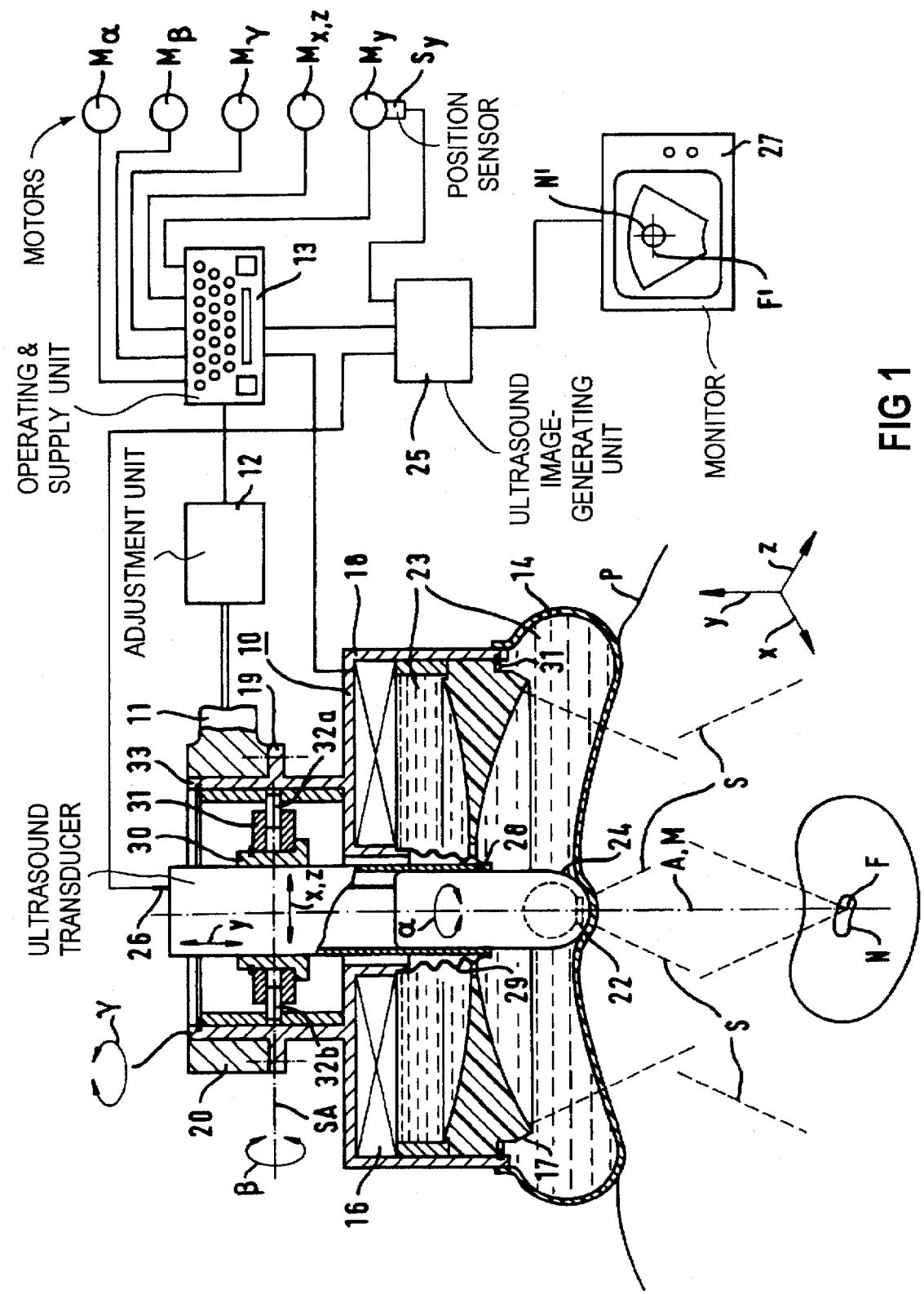
FIG. 1 is a schematic illustration of an inventive therapy apparatus.

As shown in FIG. 1, the inventive therapy apparatus has a source of focussed acoustic waves generally referenced 10 that is attached via a holder 11 to a schematically indicated adjustment unit 12. This allows the adjustment of the source 10 in the directions of the axes x, y, z of the spatial coordinate system indicated in FIG. 1. An operating and supply unit 13 is connected to the adjustment unit 12, this unit 13 containing all of the components required for the operation of the source 10 and being provided with a keyboard for operating the therapy apparatus. The source 10 lies against the body surface of a patient P with a coupling cushion 14 in order to be able to introduce the focussed acoustic waves generated during operation of the therapy apparatus into the body of the patient P in which, for example, a kidney stone N is located.

As can be seen from FIG. 1, the source 10 contains an electromagnetic pressure pulse source 16 (not shown in greater detail) and an acoustic positive lens 17. The positive lens 17 focusses the pressure pulses emanating from the pressure pulse source 16 onto a focus F, the latter being a spatial focus zone in practice. The focus F lies on the acoustic axis A of the source 10 that coincides with the middle axis M of the source 10, with reference to which the source 10 is approximately dynamically balanced. The pressure pulse source 16 and the positive lens 17 are accepted in a housing 18 that has an end remote from the pressure pulse source 16 closed liquid-tight with the elastic, flexible coupling cushion 14. The pressure pulse source 16 is, for example, an electromagnetic pressure pulse source as disclosed in terms of structure and function in European Applications 0 188 750 and 0 301 360 that generates acoustic shock waves as pressure pulses. The high-voltage pulse generator required for the operation of the pressure pulse source 16 is a component of the operating and supply unit 13 to which the pressure pulse source 16 is connected via an appropriate line.

At its other end neighboring the pressure pulse source 16, the housing 18 has a mounting flange 19 that secures the source 10 to a mounting ring 20 of the carrier 11, for example with screws, (only the center lines of two screws being indicated with broken lines in FIG. 1).

The space situated between the pressure pulse source 16 and the positive lens 17 as well as the space situated between the positive lens 17 and the coupling cushion 14 are each filled with an acoustic propagation medium. In the described exemplary embodiment, both spaces contain the same acoustic propagation medium, namely water 23, since they are in communication with one another via a central opening of the positive lens 17. These two spaces, however, can be separated from one another, differing from the described exemplary embodiment. They can then contain different acoustic propagation media.

The positive lens 17 is a biconcavely shaped solid lens that is formed of a material, for example polystyrol, in which the sound propagation speed is higher than in the water 23 provided as acoustic the propagation medium.

The source 10 has a central opening that extends both through the floor of the housing 18 and as through the pressure pulse source 16 and the positive lens 17. A diagnostic ultrasound applicator 24 is accepted in this opening, this applicator 24 being a component part of an ultrasound locating means that, in addition to containing the diagnostic ultrasound applicator 24, contains a conventionally constructed ultrasound image-generating unit 25 to which the ultrasound applicator 24 is connected via a line 26. A monitor 27 for displaying the generated ultrasound images is connected to the ultrasound image-generating unit 25.

The ultrasound applicator 24 is a B-scan sector applicator with which a circular sector-shaped body slice of the patient P can be scanned, the boundaries thereof being indicated with broken lines in FIG. 1 and being referenced S. A diagnostic ultrasound transducer 22 for generating and receiving ultrasound waves that is indicated with broken lines in FIG. 1 is contained in the ultrasound applicator 24 in a known way; the ultrasound transducer 22 emits ultrasound waves in the form of a diagnostic ultrasound beam. For generating ultrasound images, the central ray of the ultrasound beam is displaced in a planar scanning surface so that it scans a body slice of a patient to be treated. The middle of the slice corresponds to the scanning surface. By means of the ultrasound applicator 24 being adjustable relative to the source 10 (as described below) the scanning surface proceeds through the focus zone F at least for a neutral position.

The ultrasound applicator 24 is accepted non-displaceably and liquid-tight in a tube 28 that is connected liquid-tight to an inwardly directed projection of the base of the housing 18, the tube 28 being connected to the projection by an accordion bellows 29.

The tube 28 is accepted so as to be axially displaceable but non-rotatable in the central bore of a retainer sleeve 30 that is in turn accepted so as to be axially non-displaceable but rotatable in the bore of a holding flange 31. With the assistance of two articulated pegs 32a and 32b, the flange 31 is pivotable around a swivelling axis SA that intersects the middle axis M at a right angle and is connected to a bearing sleeve 22 displaceable in the direction of the swivelling axis SA. This bearing sleeve 33 is accepted in the bore of the mounting flange 19 so as to be rotatable around the middle axis M but axially non-displaceable. It thus becomes clear that 1. the ultrasound applicator 24 with the ultrasound transducer 28 together with the tube 28 is axially displaceable in both directions along the middle axis this being indicated by the double arrow y;
2. the ultrasound applicator 24 with the ultrasound transducer 22 together with the tube 28 and the retainer sleeve 30 is rotatable in both directions around the middle axis M, this being indicated by the curved double arrow α;
3. the ultrasound applicator 24 with the ultrasound transducer 22 together with the tube 28, the retainer sleeve 30 and the holding flange 31 is pivotable around the swivelling axis SA, this being indicated by the curved double arrow β;
4. the ultrasound applicator 24 with the ultrasound transducer 22 together with the tube 28, the retainer sleeve 30 and the holding flange 31 is displaceable in the respectively set direction of the swivelling axis SA in a plane parallel to the x-axis and z-axis, this being indicated by the double arrow xz; and
5. the bearing sleeve 33 together with the holding flange 31, the retainer sleeve 30, the tube 28 and the ultrasound applicator 24 with the ultrasound transducer 22 is rotatable around the middle axis M, so that the swivelling axis SA can be turned around the middle axis M. This is indicated by the curved double arrow γ that is connected to the bearing sleeve 33 via a reference line.

Motors, $M_\alpha$, $M_\beta$ and $M_\gamma$ as well as $M_y$ and $M_{xz}$, which are preferably electric motors, are provided for executing these adjustment motions, these motors being connected to the operating and supply unit 13 and being driven thereby. Gearings and the like that may be required in order to effect the adjustment motions with the motors are not shown in FIG. 1.

The motor $M_y$, for example, has an inductively acting position sensor S allocated to it that, with reference to the y-direction, emits a signal corresponding to the position of the ultrasound applicator 24 relative to the pressure pulse source 16. This signal is supplied to the ultrasound image-generating unit 25.

Taking the signal of the position sensor $S_y$ into consideration, the image generating unit 25 mixes a mark F' that shows the center of the focus zone into the signal displayed on the monitor 27, so that it is possible—on the basis of the ultrasound image—to align the source 10 relative to the body of the patient P such that the kidney stone N is located in the focus zone. This occurs when the mark F' in the ultrasound image coincides with the image N' of the kidney stone.

In a known way, the adjustability of the ultrasound applicator 24 in the y-direction serves to permit the ultrasound applicator 24 to be placed against the body surface of the patient P with the coupling cushion 14 in the way shown in FIG. 1, as is required for a good image quality. Further, in combination with the rotatability around the middle axis M in the β-direction and/or the γ-direction. The adjustability of the ultrasound applicator 24 in the y-direction serves the purpose of aligning the ultrasound applicator 24 before the actual locating procedure in a way that corresponds best to the anatomical conditions of the respective treatment case.

Moreover, all of these adjustment possibilities serve to improve the image quality of the ultrasound images generated with the ultrasound locating means. Although larger adjustment motions are required as a rule in conjunction with the above-described alignment of the ultrasound applicator, the adjustment motions that ensue for improving the image quality of the ultrasound images are very small, as shall be described below.

For improving the image quality of the ultrasound images generated with the ultrasound locating means, it can be sufficient to displace the scanning surface relative to the source 10 in the sense of an oscillating motion such that the different scanning surfaces arising as a result of this displacement are contained within a body slice of the patient P that belongs to a neutral position of the scanning surface, while insuring that the maximum displacement of the scanning surface, i.e. the stroke of the oscillating motion, does not exceed (or at least does not significantly exceed) the image resolution of the ultrasound images measured in the direction of the displacement. In case greater displacement is necessary, the displacement as a maximum should not exceed or at least not substantially exceed twice the image resolution measured in the direction of displacement. Preferably, the maximum displacement does not exceed twice the image resolution measured in the direction of displacement by more than 20%. As already explained, the poorer image quality of the stationary ultrasound images of therapy apparatus of the prior art can be improved in this way because stationary speckles are avoided.

The frequency of the oscillating motion is at most equal to the image repetition frequency with which the ultrasound locating means generates the ultrasound images. In this way, it is assured that each ultrasound image represents the entire range of displacement of the scanning surface. In order to enable the required matching of the frequency of the oscillating motion and the image repetition frequency, the operating and supply unit 13 and the image-generating unit 25 are connected to one another via an appropriate line.

The operating and supply unit 13 drives the motors $M_\alpha$, $M_\beta$, and $M_{65}$ as well as $M_y$ and $M_x$ such that, given deactivation of the oscillating motion, the scanning surface assumes its neutral position and such that, given activation of the oscillating motion, the oscillating motion of the scanning surface ensues around its neutral position as the middle position.

The manner by which the displacement of the scanning surface ensues in detail is described below with reference to FIGS. 2 through 8.

Figure 2:
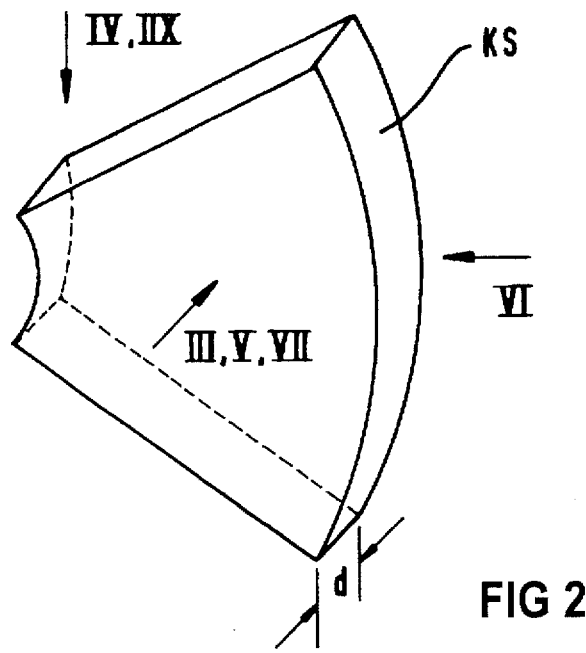
FIG. 2 is a schematic, perspective view of a body slice that can be imaged with the ultrasound locating means by displacing the central ray of the diagnostic ultrasound beam in a scanning surface corresponding to a neutral position.
Figure 3:
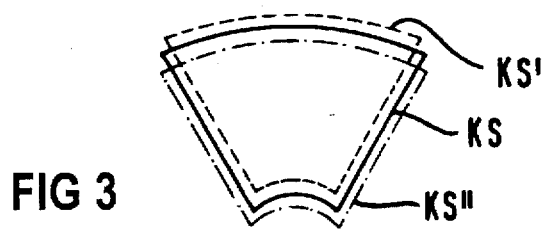
FIGS. 3–8 respectively show schematically illustrated views of the body slices that can be scanned for various forms of the displacement of the scanning surface, closing viewing directions indicated by arrows III through VIII in FIG. 2.

FIG. 2 shows the circular sector-shaped body slice KS that can be scanned with the ultrasound transducer 22 of the ultrasound applicator 24 when the diagnostic ultrasound beam that can be generated with the ultrasound transducer 22 is displaced in a planar scanning surface that corresponds to the middle plane of the body slice KS. The thickness d of the body slice KS thereby corresponds to the image resolution measured transversely relative to the scanning surface. This is constant in the schematic illustration of FIG. 2.

In order to be able to effect the displacements of the scanning surface required for improving the image quality, the operating and supply unit 13 drives the motor $M_y$ in a first operating mode selectable with the keyboard thereof such that the motor $M_y$ displaces the ultrasound applicator 24, and thus the ultrasound transducer 22 contained therein, back and forth in an oscillating motion in the y-direction. For the corresponding displacement of the scanning surface, the body slice KS that can be scanned in the neutral (middle) position (plane) is schematically shown with solid lines in FIG. 3 and the respective body slices KS' and KS" that can be scanned in the two extreme positions of the scanning surface are schematically shown therein respectively with broken and dot-dash lines. It becomes clear that the scanning surface proceeds through the focus zone F for arbitrary positions.

In another operating mode selectable with the keyboard, the operating and supply unit 13 drives the motor $M_x$ such that it displaces the ultrasound applicator 24, and thus the ultrasound transducer 22 contained therein, back and forth in the direction of the swivelling axis SA in the sense of an oscillating motion. Different forms of the displacement of the scanning surface can be achieved dependent on the angular position into which the ultrasound applicator 24 is turned by the motor $M_\alpha$ relative to the retainer sleeve 30.

Figure 4:
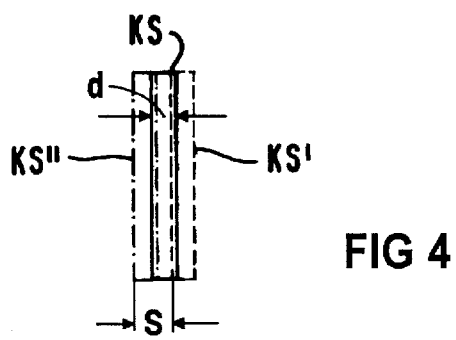
Figure 5:
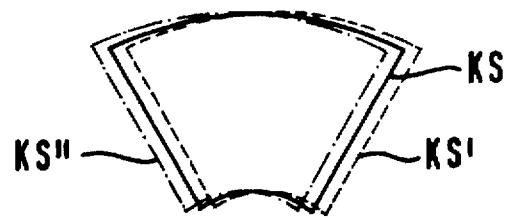

When the swivelling axis SA resides at a right angle relative to the scanning surface, then this is displaced in the way illustrated in FIG. 4. When, by contrast, the swivelling axis SA runs parallel to the scanning surface, then this is displaced in the way shown in FIG. 5. When the swivelling axis SA describes an angle with the scanning surface that differs from 0° and differs from 90° and differs from 180° and whole multiples of these angles, then intermediate forms of the displacement of the scanning surface are achieved. In FIGS. 4 and 5 as well the body slice KS that can be scanned for the neutral position, and thus the middle position of the scanning surface, is shown in solid lines and the body slices KS' and KS" that can be scanned in the two extreme positions of the scanning surface are schematically shown respectively with broken and dot-dash lines. It is clear that the scanning surface proceeds through the focus zone F for arbitrary positions only form the with of displacement shown in FIG. 5. This is only true of the neutral position of the scanning surface in the case of the form of displacement shown in FIG. 4. In FIG. 4 in addition to the image resolution d the amplitude of displacement of the scanning surface is shown and referenced with s, with s being approximately twice the resolution d.

Figure 6:
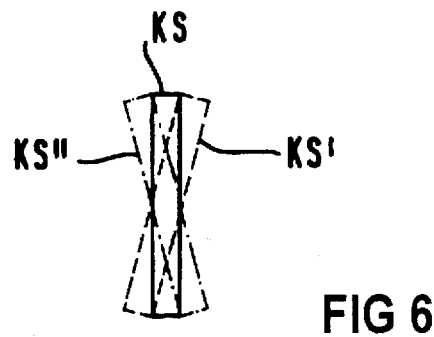

In a further operating mode selectable with the keyboard thereof, the operating and supply unit 13 drives the motor $M_\alpha$ such that it swivels the ultrasound applicator 24, and thus the ultrasound transducer 22 contained therein back and forth in an oscillating motion in the α-direction. The corresponding displacement of the scanning surface is schematically indicated in FIG. 6, whereby the body slice KS that can be scanned for the neutral position, and thus the middle position of the scanning surface is again shown in solid lines and the body slices KS' and KS" that can be scanned in the two extreme positions of the scanning surface are again schematically shown respectively with broken and dot-dash lines. It becomes clear that the scanning surface proceeds through the focus zone F for arbitrary positions.

Figure 7:
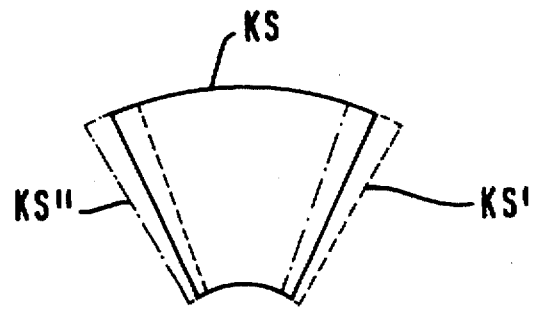
Figure 8:
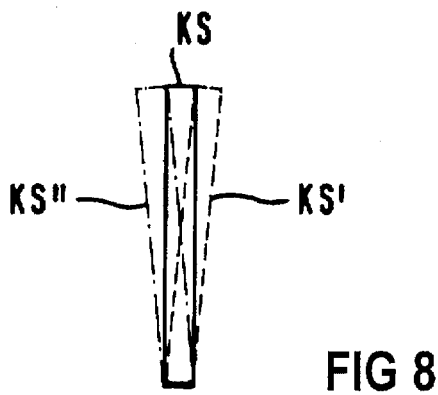

In an additional operating mode selectable with the keyboard, the operating and supply unit 13 drives the motor $M_\beta$ such that it displaces the ultrasound applicator 24, and thus the ultrasound transducer 22 contained therein back and forth around the swivelling axis SA in the sense of an oscillating motion. Different forms of the displacement of the scanning surface can be achieved dependent on the angular position into which the ultrasound applicator 24 is turned relative to the retainer sleeve 30 with the motor $M_{60}$. When the swivelling axis SA resides at a right angle relative to the scanning surface, then this is displaced in the way illustrated in FIG. 7. When, by contrast, the swivelling axis SA runs parallel to the scanning surface, then this is displaced in the way shown in FIG. 8. When the swivelling axis SA describes an angle with the scanning surface that differs from 0° and differs from 90° and differs from 180° and whole multiples of these angles, then intermediate forms of the displacement of the scanning surface are achieved. In FIGS. 7 and 8 as well, the body slice KS that can be scanned for the neutral position, and thus the middle position of the scanning surface, is shown in solid lines and the body slices KS' and KS" that can be scanned in the two extreme positions of the scanning surface are schematically shown respective with broken and dot-dash lines. It is clear that the scanning surface proceeds through the focus zone F for arbitrary positions only for the form of displacement shown in FIG. 7. This is only true of the neutral position of the scanning surface in the case of the form of displacement shown in FIG. 8.

It should again be noted that the maximum displacement of the scanning surface does not significantly exceed (if at all) twice the resolution of the ultrasound images measured in the direction of the displacement. Despite the displacement of the scanning surface, the precision of the locating is not negatively influenced since, so to speak, the same body slice is always displayed in the individual ultrasound images despite the displacement of the scanning surface.

In the operating modes illustrated in FIGS. 3 through 8, the displacement of the scanning surface respectively ensues such that the different scanning surfaces are at least partly contained in the body slice KS belonging to the respective neutral position of the scanning surface. In the operating modes of FIGS. 4, 6 and 8, there is also the possibility of effecting the displacement of the scanning surface such that the different scanning surfaces are respectively completely contained within the body slice KS belonging to the corresponding neutral position of the scanning surface. The maximum displacement of the scanning surface then cannot be greater than the resolution of the ultrasound images measured in the direction of the displacement.

In FIGS. 3 to 8, for the sake of simplicity, the scanning surfaces are shown as plane surfaces, though a continuous oscillating movement of the scanning surface is effected, which in reality results in a curved scanning surface. A plane surface, however, is a good approximation as the amplitude of the oscillating movement is in the order of magnitude of several millimeters only.

It was assumed above that the image resolution, particularly in the direction of the displacement of the scanning surface, is constant over the entire ultrasound image. This need not necessarily be the case in practice. If a constant image resolution is not present, then, given slight fluctuations of the image resolution, the average image resolution can be utilized as a criterion for the displacement of the scanning surface. Given greater fluctuations of the image resolution, either the minimum image resolution or the image resolution existing in a diagnostically especially relevant area, for example the area surrounding the focus zone F in the described exemplary embodiment, can be utilized as a criterion for the displacement of the scanning surface.

In the embodiment shown in FIG. 1, the displacement of the scanning surface relative to the source 10 ensues mechanically. As indicated in FIG. 1 with broken lines, the ultrasound applicator 24 can therefore contain an ultrasound transducer (or a plurality of ultrasound transducers in a known way) attached to a rotor (referred to as a mechanical sector scanner) or can contain an ultrasound applicator preferably implemented as a linear array (linear arrangement of ultrasound transducer elements) that is operated (by the arrangement being driven phase-offset) in the fashion of a phased array (electronic sector scanner).

The forms of displacement of the scanning surface shown in FIGS. 5 and 7 can also be realized in an electronic way with the assistance of a linear array operated in the fashion of a phased array. The displacement of the scanning surface then ensues electronically rather than mechanically.

The forms of displacement of the scanning surface shown in FIGS. 4, 6 and 8 can also be electronically realized; however, a matrix-like array of ultrasound transducers that is driven in the fashion of a phased array is then required. A mechanical displacement would have to additionally ensue if a linear array is used.

Figure 9:
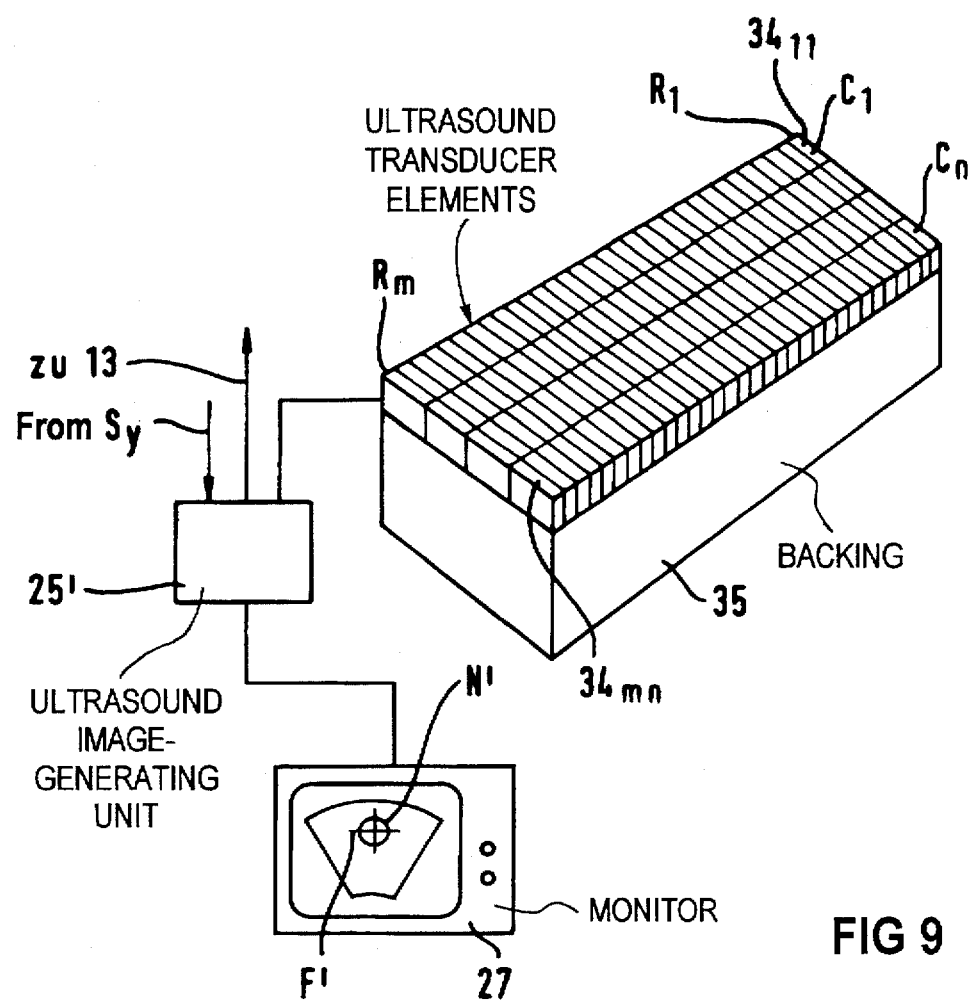
FIG. 9 is a schematic illustration of a detail of another therapy apparatus of the invention.

FIG. 9 shows a suitable matrix-like array of ultrasound transducer elements that can be stationarily attached in the ultrasound applicator 24 instead of the ultrasound transducer attached to a rotor in FIG. 1. The ultrasound transducer elements $34_{11}$ through $34_{mn}$, of the array are arranged in m rows, for example 256 rows $R_1$ through $R_m$ of n columns, for example 4 columns $C_1$ through $C_n$ each. They are attached in a known way on a backing (carrying member) 35 and are provided with electrodes for electrical contacting in a way that is likewise known and is therefore not shown.

As schematically indicated in FIG. 9, the ultrasound transducer elements $34_{11}$ through $34_{mn}$ are connected to an ultrasound image-generating unit 25' that corresponds in function to the ultrasound image-generating unit of FIG. 1 apart from the fact that it is not fashioned for collaboration with a mechanical sector scanner but with a matrix-like array of ultrasound transducer elements. This collaboration, which allows the ultrasound image-generating unit 25' to drive the matrix-like array of ultrasound transducer elements in the manner of a phased array, is not limited only to deflecting the diagnostic ultrasound beam generated with the matrix-like array of ultrasound transducer elements in the way required for generating ultrasound images, but also allows the array to be driven as required for the displacement of the scanning surface according to 3 through 8. The form of the displacement can be selected with the operating and supply unit 13 connected to the ultrasound image-generating unit 25'.

Independently of whether the displacement of the scanning surface ensues mechanically or electronically, it will usually be expedient to implement the displacement in the form of a continuously oscillating motion. It is also fundamentally possible, however, to provide the displacement in the form of a step-by-step motion. This can be accomplished, for example, in the embodiment shown in FIG. 1, by the operating and supply unit 13 correspondingly driving the motors $M_\alpha$, $M_\beta$ and $M_\gamma$ as well as $M_y$ and $M_z$ according to the selection of a corresponding operating mode. In this case, the ultrasound image-generating means generates the ultrasound images with such an image repetition frequency such that each ultrasound image represents more than one position of the scanning surface.

It should also be noted that combinations of the forms of displacement illustrated in FIGS. 3 through 8 are also possible for the displacement of the scanning surface.

Whereas the scanning surface is planar in the exemplary embodiment of FIG. 1, there is also the possibility of realizing non-planar scanning surfaces, for example curved scanning surfaces, given the use of an ultrasound transducer constructed as a matrix-like array.

Moreover, it should be noted that it can be expedient also to allocate position sensors to the motors $M_\alpha$, $M_\beta$ and $M_\gamma$ and $M_z$, the output signals of these position sensors being supplied to the operating and supply unit 13, for example in order to be able to designationally set a defined neutral position of the scanning surface. It can also be expedient in this context to supply the output signal of the position sensor $S_y$ to the operating and supply unit 13.

In the described exemplary embodiment, the source 10 is adjusted relative to the patient P. Of course, the source 10 can alternatively remain stationary and the patient P can be adjusted relative to the source insofar as the patient is supported on a patient bearing mechanism that is adjustable in a suitable way. Further, there is the possibility of achieving the required adjustment of source 10 and patient P relative to one another by moving both the source 10 and the patient P.

In the described exemplary embodiment, the positive lens 17 has a fixed focal length, however, there is also the possibility of employing a vario lens, i.e. a lens with a variable focal length. In this case, suitable measures must be undertaken to assure that the mixing-in of the marks F' and F" ensues taking the set focal length of the vario lens into account.

In the described exemplary embodiment, the ultrasound locating means operates in a sector scan mode. When employing a linear array operated as a phased array or when employing a matrix-like array, however, it is also possible within the scope of the invention to operate the ultrasound locating means in what is referred to as the linear scan mode. Instead of a circular sector-shaped body slice, a rectangular body slice is then imaged in the ultrasound image generated with the ultrasound locating means.

In the above-described exemplary embodiment, the source 10 contains an electromagnetic pressure pulse source. The inventive therapy apparatus, however, can alternatively contain some other type of pressure pulse source, for example a piezoelectrically acting pressure pulse source. Moreover, there is the possibility of providing some other source of acoustic waves instead of a pressure pulse source, for example an ultrasound source that generates ultrasound in the form of continuous sound, ultrasound bursts or ultrasound pulses. Particularly in this case, there is the possibility of utilizing the therapy apparatus for hyperthermic treatment methods. It becomes clear at the same time that inventively fashioned therapy apparatus can be utilized not only for the lithotripsy as described in conjunction with the exemplary embodiment but also for other medical purposes.

Although the invention has been described with respect to preferred embodiments, it is not to be so limited as changes and modifications can be made therein which are within the full intended scope of the invention as defined by the appended claims.

We claim as our invention:

1. A therapy apparatus comprising:

a source of therapeutic acoustic waves;

a diagnostic ultrasound transducer which emits a diagnostic ultrasound beam directed at a subject to be treated, said diagnostic ultrasound beam having a central ray, and said diagnostic ultrasound transducer also receiving ultrasound waves reflected from said subject;

means for operating said ultrasound transducer for displacing said central ray in a scan surface for scanning a body slice of said subject, said body slice having a middle surface corresponding to said scanning surface;

means for generating and displaying a sequence of ultrasound images from the ultrasound waves received by said diagnostic ultrasound transducer; and adjustment means for, during the generation and display of said ultrasound images, continually displacing said scanning surface relative to said source of therapeutic acoustic waves for producing a maximum displacement of said scanning surface relative to a neural position of said scanning surface which does not substantially exceed twice an image resolution of said ultrasound images measured in a direction of the displacement of the scanning surface.

2. A therapy apparatus as claimed in claim 1 wherein said adjustment means comprises means for displacing said scanning surface relative to said source for scanning different scanning surfaces which are at least partly contained within a body slice associated with said neutral position.

3. A therapy apparatus as claimed in claim 1 wherein said adjustment means comprises means for displacing said scanning surface step-by-step and wherein said means for generating and displaying a sequence of ultrasound images comprises means for generating said ultrasound images within image repetition frequency selected so that a displayed ultrasound image represents more than one position of said scanning surface.

4. A therapy apparatus as claimed in claim 1 wherein adjustment means comprises means for oscillating said scanning surface relative to said source of acoustic waves.

5. A therapy apparatus as claimed in claim 4 wherein said means for generating and displaying a sequence of ultrasound images comprises means for generating said ultrasound images within image repetition frequency which is at least equal to a frequency of oscillation of said scanning surface.

6. A therapy apparatus as claimed in claim 4 wherein said adjustment means comprises means for oscillating said scanning surface around said neutral position as said middle position.

7. A therapy apparatus as claimed in claim 1 wherein said adjustment means comprises means for mechanically displacing said diagnostic ultrasound transducer relative to said source.

8. A therapy apparatus as claimed in claim 1 wherein said diagnostic ultrasound transducer comprises a phased array, and wherein said adjustment means comprises means for driving said phased array during the generation of ultrasound images so as to displace said scanning surface relative to said source of acoustic waves.

9. A therapy apparatus as claimed in claim 1 wherein adjustment means comprises means for displacing said scanning surface relative to said source in a substantially straightline motion.

10. A therapy apparatus as claimed in claim 1 wherein said adjustment comprises means for displacing scanning surface relative to said source of acoustic waves in a swiveling motion.

11. A therapy apparatus as claimed in claim 1 wherein said scanning surface is substantially planar.

12. A therapy apparatus as claimed in claim 11 wherein said adjustment means comprise means for displacing said scanning surface relative to said source of acoustic waves in a substantially straightline motion in a direction proceeding substantially parallel to the scanning surface in the neutral position.

13. A therapy apparatus as claimed in claim 11 wherein said adjustment means comprise means for displacing said scanning surface relative to said source of acoustic waves in a substantially straightline motion in a direction proceeding substantially transverse to the scanning surface in the neutral position.

14. A therapy apparatus as claimed in claim 11 wherein said adjustment means comprise means for displacing said scanning surface relative to said source of acoustic waves in a swiveling motion around an axis proceeding substantially parallel to said scanning surface in said neutral position.

15. A therapy apparatus as claimed in claim 11 wherein said adjustment means comprise means for displacing said scanning surface relative to said source of acoustic waves in a swiveling motion around an axis proceeding substantially transverse to said scanning surface in said neutral position.

16. A therapy apparatus as claimed in claim 1 wherein said source of therapeutic acoustic waves comprises means for generating therapeutic acoustic waves focused onto a focus zone, said scanning surface proceeding through said focus zone at least in said neutral position.

* * * * *